United States Patent [19]

Sigler

[11] Patent Number: 4,973,248

[45] Date of Patent: Nov. 27, 1990

[54] DELIVERY SYSTEM FOR DENTINAL/ENAMEL ADHESIVE MATERIALS

[75] Inventor: Timothy Sigler, St. Joseph, Mo.

[73] Assignee: Myron International, Inc., Kansas City, Kans.

[21] Appl. No.: 281,677

[22] Filed: Dec. 9, 1988

[51] Int. Cl.$^5$ .............................................. A61C 5/04
[52] U.S. Cl. ..................................................... 433/90
[58] Field of Search ....................... 433/81, 88, 90, 80; 604/201, 205, 232, 236, 238

[56] References Cited

U.S. PATENT DOCUMENTS

| | | | |
|---|---|---|---|
| 1,118,040 | 11/1914 | Mulder | 604/236 X |
| 3,130,724 | 4/1964 | Higgins et al. | 604/201 |
| 3,295,525 | 1/1967 | Evers et al. | 604/232 X |
| 3,462,840 | 8/1969 | Ellman | 433/90 |
| 3,480,014 | 11/1969 | Callahan | 604/201 X |
| 3,557,778 | 1/1971 | Hughes | 604/236 X |
| 3,618,216 | 11/1971 | Jaeger | 433/90 |
| 3,931,815 | 1/1976 | Takatsuki | 604/205 X |
| 4,303,069 | 12/1981 | Cohen | 604/201 |
| 4,445,895 | 5/1984 | Margulies | 604/201 X |
| 4,569,662 | 2/1986 | Dragan | 433/89 |

FOREIGN PATENT DOCUMENTS 1192065  8/1985  Canada ................................ 433/90

*Primary Examiner*—John J. Wilson
*Assistant Examiner*—Nicholas D. Lucchesi
*Attorney, Agent, or Firm*—Hovey, Williams, Timmons & Collins

[57] ABSTRACT

A delivery system for dispensing liquid dental materials is provided which enables a dentist or dental technician to efficiently store and safely apply materials such as etchants and adhesives through use of a modified syringe assembly. The liquid dental material for application to a tooth surface and a protective gas bubble are carried within a carpule assembly which includes a plunger extending rearwardly from a glass carpule. A needle preferably having a blunt application tip is mounted in fluidic communication with the liquid and passes through the liquid delivery end of the carpule. The carpule is sealed to prevent the entry of air therein or the inadvertent expression of liquid therefrom and is adapted for use with a series of disposable needles. In one embodiment, the invention is provided with a syringe barrel and an application needle is removably mounted thereon. The needle is provided with a long, rearwardly extending tubular portion for penetrating a sealing membrane on the carpule and communicating with the liquid dental material. The plunger is engaged with the carpule so that the carpule may be withdrawn from the syringe barrel by pulling on the plunger without pulling air into the carpule. Alternatively, the carpule may be provided with a check-valve adapted to receive a needle thereon so that air is prevented from entering the carpule and eliminating the need for a syringe barrel.

16 Claims, 2 Drawing Sheets

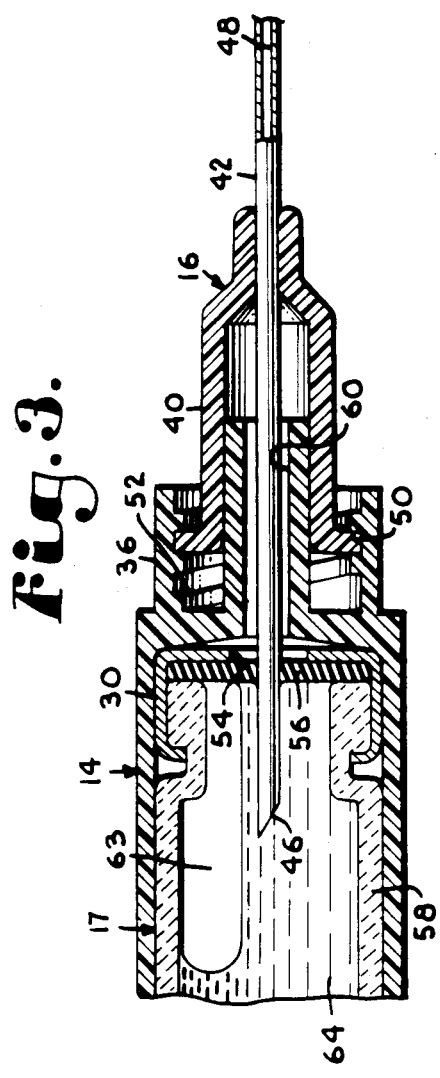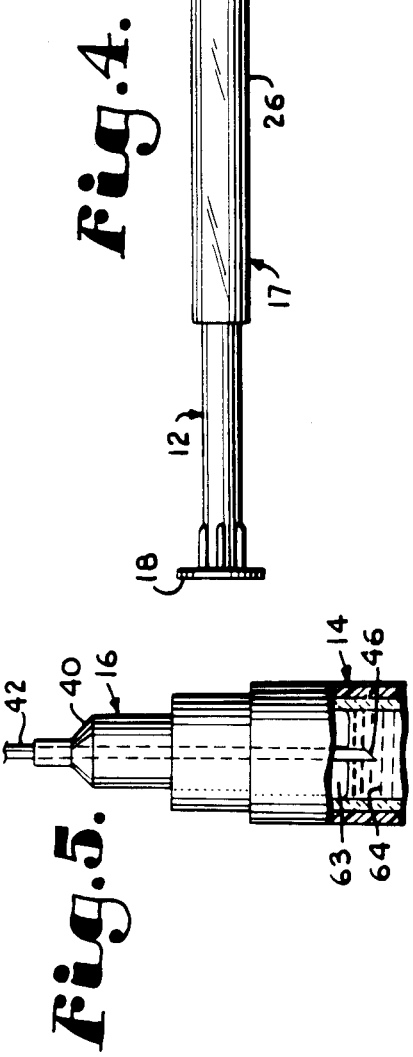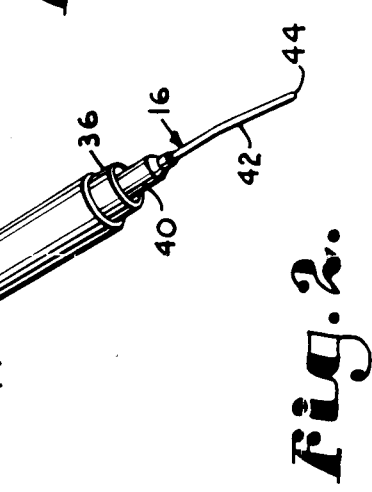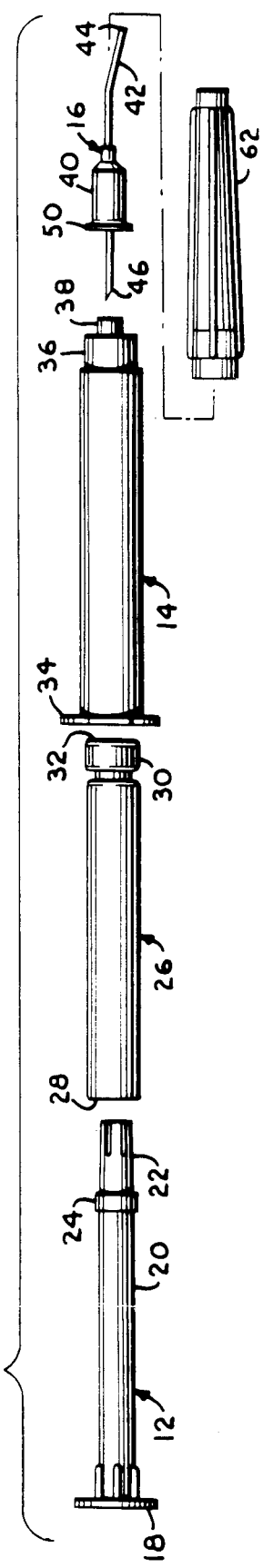

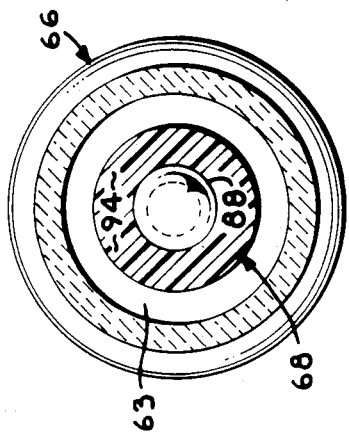
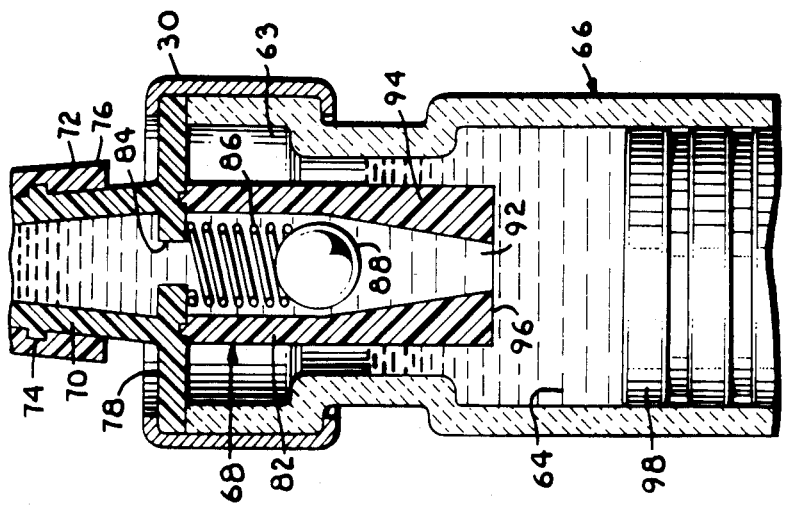
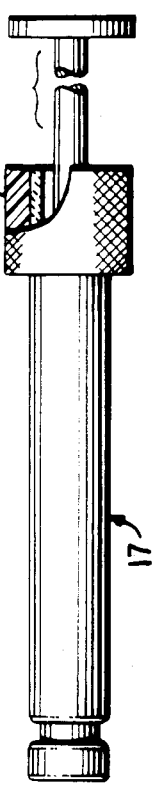
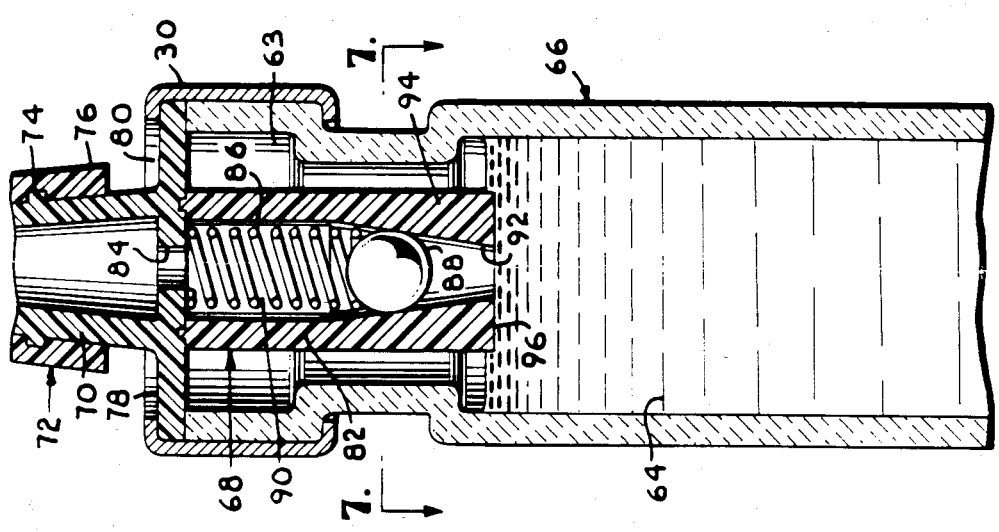

DELIVERY SYSTEM FOR DENTINAL/ENAMEL ADHESIVE MATERIALS

BACKGROUND OF THE INVENTION

1. Field of the Invention

This invention relates to an economical delivery system for the application of liquid dental materials, especially adhesive materials, during restorative dental treatments. More particularly, the invention pertains to a safe, easy to use application system wherein the adhesive materials are maintained in dental carpules which are designed to eliminate the possibility of inadvertent injection of the adhesive materials into tissue. Moreover, the system includes specialized structure for maintaining a bubble of protective gas within the carpules while at the same time insuring that tubular liquid application structure associated with the carpule remains in constant communication with the liquid within the carpule; in this manner, expression or leakage of the protective gas from the carpule is inhibited during use of the system.

2. Description of the Prior Art

Restorative dentistry is an evolving field wherein patients with damaged, diseased, disfigured or discolored teeth may have the teeth resurfaced or reconstructed to an optimum shape and appearance. In recent years, use of porcelain dental restorations has achieved a considerable degree of commercial success, particularly in view of the enhanced aesthetic effects which can be obtained using porcelain restorations. For example, porcelain restorations may be applied in the forms of crowns, inlays, or veneers.

In the application of porcelain veneers, practitioners often etch either the teeth to be restored or the undersides of the restorations (or both) using an acid solution. Further, use is often made of dentinal or enamel lining or adhesive materials in order to firmly bond the restorations to teeth. One such method which has achieved significant commercial acceptance is disclosed in U.S. Pat. No. 4,654,007 entitled "Porcelain Dental Restoration Method".

It has also been proposed in the past to employ adhesive materials such as pyromellitic dianhydride dimethacrylate (PMDM) for attachment of porcelain restorations. PMDM must be continually exposed to oxygen during storage and prior to use, else it will prematurely polymerize. By the same token, acidic surface conditioning etching solutions containing a combination of N-phenyl glycine (NPG) and $HNO_3$, or alternatively phosphoric acid, used in conjunction with PMDM should be protected from the adverse affects of air prior to actual application. Accordingly, it has been suggested to package PMDM and associated acidic surface conditioning etching agents in respective dental carpules each containing a bubble of protective gas (oxygen in the case of PMDM, and an inert gas such as argon in the case of the surface conditioner etchant).

While use of carpules with protective gas bubbles would appear to represent a complete solution to the storage problem, a number of practical difficulties have arisen. First, the dental carpules heretofore employed for PMDM and surface conditioner etchant are of the standard size and shape heretofore used for injectable materials such as dental anesthetics. Such carpules are sized to fit within a conventional dental injection syringe found in every dentist's office. As can be appreciated, it would be hazardous indeed to supply PMDM and acidic surface conditioner etchants in these standard carpules, because of the real danger that the PMDM and/or surface conditioner etchant could be inadvertently injected using a conventional dental syringe. For this reason, packaging of PMDM and etchants in completely standard dental carpules has not been approved.

Furthermore, if standard dental carpules containing PMDM or surface conditioner etchant are employed with conventional dental syringes, there is a very real possibility that the protective gas bubbles within the carpules would be immediately ejected or expressed upon initial use. This stems from the fact that the dental syringes are provided with only very short membrane-puncturing tubular members designed to pass into the dental carpules to the minimum extent necessary to establish fluid communication between the carpules and the injection needles used with the syringe. As will be readily seen, use of long membrane-puncturing tubes would prevent full use of the anesthetic or other injectable material within the carpule.

Accordingly, there is a real and heretofore unsatisfied need in the art for an improved system particularly designed for precise application of liquid dental materials such as adhesives and etchants which are suitable for repeated use on a succession of patients while eliminating the possibility of inadvertent tissue injection and/or loss of protective gas.

SUMMARY OF THE INVENTION

The problems outlined above are in large measure solved by the delivery system in accordance with the present invention. The delivery system as provided herein provides a simple, easy to use adhesive delivery system which is inexpensive to construct and effectively and efficiently distributes liquid dental materials through a syringe type system while avoiding the hazards of inadvertent substitution into a dental syringe designed for administering dental injectables. As used herein, the term "liquid dental materials" is to be understood to include both etching and bonding agents to be applied to the dentin or enamel of a tooth.

The delivery system hereof includes a glass carpule adapted to receive liquid dental materials therein. A plunger extends rearwardly from a first end of the carpule while the second, liquid delivery end of the carpule is provided with a sealing member to resist contamination of the dental adhesive fluid by extraneous gases. The carpule assembly contains a liquid dental material and a bubble of a protective gas for isolating the liquid against exposure to air. The plunger assembly extends rearwardly from the carpule in order to immediately identify and distinguish the carpules containing adhesives and etchants from dental injectables which may be inserted into a standard dental injectable syringe. The carpule with the plunger thereon will not ordinarily fit into a conventional dental injection syringe. The carpule carries an application means, such as a needle, including a rearwardly extending tubular portion of sufficient length to permit expression of the fluid without expression or leakage of the protective gas.

Because the delivery system hereof is not designed for injecting the fluid into tissue but rather simply delivering the fluid adhesive to the surface of a tooth, the application needle is provided with a blunt end as a further means of avoiding inadvertent injection. The rear end of the needle may be provided with a sharpened tip so it may puncture and penetrate a self-sealing resilient membrane when the carpule is inserted in the syringe. Thus, the carpule may be used repeatedly as only a small portion of adhesive is ordinarily applied. A different application needle would ordinarily be provided for each patient, and a disposable syringe barrel may be provided for carrying the carpule therewithin and for mounting the application needle thereon.

To prevent contamination of the dental adhesive within the carpule, the gas bubble is supplied within the carpule to act as a buffer against the entry of air into the interior of the carpule. The gas bubble may be an inert gas, such as argon, or alternatively any other gas which provides the desired protective effects according to the type of adhesive within the carpule. The tubular needle is configured so that the rearwardly extending portion remains in communication with the liquid within the carpule during various orientations of the delivery system in order to ensure that a substantial part of the gas bubble remains within the carpule while the fluid adhesive is being expressed.

In an alternative embodiment, the carpule may be provided with a one-way valve. In this manner, the valve may be especially configured to receive a needle directly thereon. The one-way valve is preferably a ball-type check valve which permits the fluid adhesive to be expressed while preventing the entry of contaminating air into the carpule.

BRIEF DESCRIPTION OF THE DRAWING

FIG. 1 is a perspective view of the delivery system hereof, showing the carpule hereof inserted within the syringe barrel;

FIG. 2 is an exploded side elevational view of the syringe components of the delivery system prior to assembly;

FIG. 3 is an enlarged, fragmentary sectional view showing the application needle and the carpule mounted to the syringe, with the posterior end of the needle penetrating the self-sealing membrane of the carpule;

FIG. 4 is side elevational view of the carpule hereof, as it would normally be supplied to the dentist, showing the plunger extending rearwardly from the posterior of the carpule;

FIG. 5 is an enlarged, fragmentary sectional view of the delivery system hereof, showing the delivery system in vertical orientation with the posterior end of the delivery needle extending just beyond the gas bubble to remain in fluid communication with the liquid adhesive material;

FIG. 6 is a vertical sectional view showing an alternate embodiment of the invention wherein a check valve is provided on the anterior end of the carpule;

FIG. 7 is a cross-sectional view along line 7—7 of FIG. 6 showing the annular space surrounding the check valve;

FIG. 8 is a vertical sectional view similar to FIG. 6 wherein force has been applied to the plunger to express liquid from the carpule through the check valve; and FIG. 9 is a fragmentary side-elevational view in partial section showing an annular collar surrounding the carpule to avert inadvertent insertion in a dental injection syringe.

DESCRIPTION OF THE PREFERRED EMBODIMENT

Referring now to the drawing, a delivery system for liquid dental materials 10 in accordance with the invention broadly includes a plunger 12 at the posterior end of the assembly 10, a syringe barrel 14 and an application needle 16 at the anterior end of the assembly 10. The plunger extends rearwardly from the syringe barrel 14 and forms part of a carpule unit 17 which is adapted for insertion into the syringe barrel 14 and contains the appropriate liquid dental material therein. The application needle 16 is removably mounted on the syringe barrel in order that it may be removed and discarded after use with each patient.

In more detail, FIG. 2 shows the delivery system 10 in an exploded view to reveal each of the components thereof. Beginning at the posterior end of the assembly 10, plunger 12 is approximately 7 cm. in length and includes a thumb rest 18 at the end of a stem 20 for the application of manual pressure to the plunger. At the anterior end of the plunger is a head 22, which is preferably made of a resilient, rubber material, which is surrounded by a seal 24 having an uncompressed diameter of about 0.8 cm. The head 22 thus engages the carpule walls 58 in a snug, sealing fit with the interior of carpule 26. Thus, seal 24 is in slidable engagement with wall 58 of carpule 26 in order to maintain a fluid-tight fitting therebetween, while enabling the plunger 12 to be slidably movable with respect to the carpule 26.

The carpule 26 is in the form of a glass tube which is designed to be filled with the appropriate liquid etching or adhesive material. Such carpules are well known in the dental art as receptacles for dental injectables such as the anesthetic xylocaine and are about 6.3 cm. in length and has an interior diameter of about 0.65 cm. The carpule is provided with a first open, posterior end 28 which is adapted to receive head 22 of plunger 12. Opposite open end 28 is second, liquid delivery, front end 32, which is encased with a metal cap 30. Cap 30 is crimped on carpule 26 for mounting rubber sealing membrane 56 thereto.

The carpule 26 is sized to be fitted in syringe barrel 14, which is of a standard, commercially available type. Syringe barrel 14 preferably includes a flange 34 extending laterally at the anterior end of the syringe barrel as an aid to grasping during use. A hub 36 projects forwardly at the anterior end of the syringe barrel 14 and surrounds projection 38 which defines an orifice therein. The hub 36 and projection 38 form what is commonly known as a Luerlock connector.

Hub 36 is internally threaded and is adapted to receive housing 40 of application needle 16 threadably therein, while the housing 40 fits over projection 38. The shaft 42 of the needle 16 is bent proximate the front end, and terminates in blunt tip 44 at the anterior end thereof. The shaft 42 extends through housing 40 and terminates in a sharpened membrane-piercing end 46 at the posterior end of a needle. The blunt tip 44 is bent at an oblique angle relative to the sharpened end 46.

As better shown in FIGS. 1 and 3, the application needle 16, carpule unit 17 and the syringe barrel 14 are fitted together as system 10. The application needle 16 is provided with a tubular shaft having a passageway 48 therethrough for communicating fluid through the shaft 42 of the needle 16. The needle 16 is threadably mounted on housing 36 by a circumferential lip 50 extending radially from the housing 40 which is threadably engaged with threads 52 of housing 36. The shaft 42 is of sufficient length that when the application needle 16 is mounted within the housing, the projection 38 extends into the interior of the housing and the sharp end 46 of the shaft 42 extends rearwardly at least 0.5 cm. into the interior of the carpule 26 and the syringe barrel.

As shown in FIG. 4, it is contemplated that the carpule 26 will be supplied as part of an integral unit 17 with plunger 12 attached to carpule 26. Thus, the plunger stem 20 and thumb rest 18 project rearwardly from the open end 28 of carpule 26 to present a distinguishing and distinguishable appearance from carpules without such plungers.

Returning to FIG. 3, when carpule 26 is supplied to the dentist, it is provided with a self-sealing membrane 56 held in place on front end 32 of carpule 26 by cap 30. The membrane 56 is preferably a self-sealing, synthetic rubber septum which is sufficiently resilient to close and present a seal around stem 42 of needle 16 once pierced by sharp end 46 and to remain fluid-tight after the shaft 42 is withdrawn. The force applied by the membrane 56 against the needle 16 and the coefficient of friction between the membrane 56 and needle 16 are such that the magnitude of the force required to shift the plunger 12 with respect to the carpule 26 is much greater than the magnitude of the force required to shift the carpule 26 with respect to the needle 16.

The shaft 42 enters through the membrane 56 through an opening 54 in metal cap 30. Projection 38 defines on orifice 60 therein and shaft 42, opening 54, and orifice 60 are in co-axial alignment when unit 10 is fully assembled. The metal cap 30 holds the self-sealing membrane 56 against the walls 58 of the carpule 26 in order to ensure a proper, fluid-tight seal. The shaft 42 of needle 16 is of a sufficient length that sharpened end 46 at all times remains in communication with the liquid adhesive contained within the walls 58 of the carpule 26 when the delivery system 10 is assembled.

A gas bubble 63 is incorporated within the carpule 26 to absorb and dilute any air which may inadvertently enter the carpule. The gas bubble 63 may be of argon or other inert protective gas (when $HNO_3$ etching agents are used as the liquid dental material 64), or $O_2$ which acts to inhibit polymerization of PMDM (when PMDM is used as liquid dental material 64). In order to preserve this gas bubble, sharpened end 46 extends a sufficient distance into the interior of the carpule 26 that it will remain in constant communication with such liquid adhesive material 64 as best shown in FIG. 3 when the delivery system is oriented in the horizontal position, and as shown in FIG. 5 when the delivery system is held in an upright, vertical position with the second, liquid delivery end 32 of the carpule 26 and the application needle 16 being above the syringe barrel 14. The sharpened end 46 extends at least 1 cm. rearwardly from the housing and 0.5 cm. into the carpule 26. It may also be seen from FIG. 3 that carpule 26 is to be sized of a diameter to fit within the interior of syringe barrel 14 such that the wall of carpule 26 is slidable with respect to the syringe barrel 14. A cap 62 is provided to mount on hub 36 over needle 16 for resisting contamination.

In an alternative embodiment, the carpule 26 may be provided with a check valve to eliminate the need for a syringe barrel.

Turning to FIG. 6, the syringe barrel has been omitted and the carpule 66 has been fitted with a one-way check valve 68. Check valve 68 is mounted on carpule 66 by cap 30 which is the same as is shown in the previous embodiment. The check valve 68 includes forward projection 70 on which a needle 72 is adapted to be fitted thereover. Projection 70 includes a rim 74 on which the needle housing 76 may be fitted. The remaining portions of the needle are substantially shown as in FIG. 2, with the bent shaft 42 and blunt tip 44 as shown in FIG. 2.

Check valve 68 also includes wall member 78 for sealing the forward end 80 of the carpule and connecting projection 70 with valve portion 82. Wall 78 is in the form of an annular ring surrounding a throat 84 through which liquid adhesive 64 may communicate.

Valve portion 82 includes teflon treated or plastic spring 86 which would not be affected by acid which is biased against front wall 78. Opposite front wall 78 is tall 88. Check valve 82 is tubular in that it includes a first, cylindrical opening 90 which then narrows into a frusto-conical opening 92 which becomes progressively more narrow in a rearward direction. The ball 88, biased by spring 86, contacts the wall 94 in sealing engagement.

As in the previous embodiment, the carpule 66 is filled with a liquid dental adhesive or etching material 64 which is protected by a gas bubble 63. The posterior end 96 of the one-way valve 68 remains in communication with liquid 64 even when the gas bubble 63 is vertically above the liquid 64.

As shown in FIG. 8, as plunger head 98 is advanced, it exerts a force on liquid 64 which in turn unseats ball 88 and compresses spring 86. The plunger head 98 may be configured with a series of annular sealing baffles in conventional manner as shown in FIG. 8, or head 22 may be used as shown in FIG. 2. Liquid adhesive 64 is thus able to pass through check valve 68, through throat 84, and into needle 72 for application to the patient's tooth. The spacial relationship between the various passages is best illustrated in FIG. 7 wherein the various passageways are shown. Ball 88 remains seated within frusto-conical opening 92 and against wall 94 until the pressure exerted on plunger 98 unseats ball 88.

FIG. 9 discloses an additional component which may be added to carpule 24 to aid in preventing inadvertent substitution of an adhesive carpule for an injectables carpule. As shown in FIG. 8, a collar 100 may be fitted onto carpule unit 17 adjacent its rear, open end 28 to provide further protection against inadvertent substitution into an ordinary syringe. The collar 100 may be of rubber or synthetic resin material for fitting into the syringe barrel 14 or alternatively onto the glass carpule 26 and thereby lie in interference with the sides of an ordinary syringe. The use of collar 100 thus requires a modified syringe barrel 14 to accommodate the carpule 17 and collar 100. A modified syringe barrel 14 includes a corresponding enlarged diameter portion at the posterior end of the barrel in order to receive the collar 100 therein with the collar 100 in frictional engagement with both the carpule 26 and the syringe barrel 14.

In operation, the delivery system as shown in FIGS. 1 though 5 are used to deliver, for example, a liquid dental material 64 such as a dental etching solution which may contain, for example, a solution of 2.5% $HNO_3$ in water and in which 4% by weight N-phenyl glycine (hereinafter NPG) has been dissolved. This solution is susceptible to degradation during storage and is mixed and stored under argon. Argon is often used to flush the empty vial to remove residual oxygen and then the acid-NPG solution is injected through the rubber sealing membrane 56 after the plunger 12 is inserted into the open end 28 of the carpule 26. This solution is normally used for etching the tooth surface. An additional liquid dental material 64 for use in the system hereof is a mixture of 5% by weight pyromellitic dianhydride dimethacrylate (hereinafter PMDM) in acetone which is used as an adhesive in bonding a porcelain dental restoration to the dentin or enamel surface of the tooth. This solution is especially stable in the presence of oxygen, and accordingly an oxygen bubble 63 is left in the carpules to inhibit polymerization of the PMDM. Again, the PMDM and acetone solution is injected into the carpule through the sealing membrane 56 with plunger 12 being withdrawn during the filling steps. The plunger 12 is of sufficient length, as shown in FIG. 2, that its overall length is greater than the carpule 26 and thus when the plunger 12 is inserted in the first, open end 28 of carpule 26, a portion of the plunger 12 always extends rearwardly from the open end 28.

The filled carpule units 17 are delivered to the dentist in the units 17 substantially as shown in FIG. 4. The dentist may use the application system 10 by mounting needle 16 on syringe barrel 14, and then inserting carpule 24 with plunger 12 thereon into the interior of the body of the syringe barrel 14. During insertion, the sharp end 46 of the needle 16 will penetrate the membrane 56 and remain in communication with the liquid 66 inside the carpule 26. Because the sharp end 46 remains in communication with the liquid 64, leakage of the protective gas 63 or entry of contaminating air through the shaft 42 is inhibited. The delivery system 10 is thus ready to use on a particular patient.

After each use, the carpule unit 17 may be easily withdrawn by pulling rearwardly on the plunger 12, as the fit between seal 24 and the walls 58 of carpule 26 is much tighter than the fit between the carpule 26 and the syringe barrel 14. Thus, by pulling on thumb rest 18, the carpule 26 shifts relative to the needle 16 mounted on the syringe barrel 14 but the plunger 12 does not shift relative to the carpule 26. As the carpule is withdrawn, the membrane 56 again closes in a sealing relationship to prevent the escape of liquid adhesive 66 or the entry of contaminating air. The gas bubble 63 remains in place to buffer and disperse any contaminating air which may enter the carpule.

After each use, the needle 16 may be discarded and a new needle substituted on the syringe 14, or both the syringe barrel 14 and needle 16 may be discarded. As the carpule contains sufficient liquid adhesive or etching material 64 for a number of applications, the ability of the membrane 56 to reseal permits retention of the carpule 26 for numerous applications and leads to more efficient use of the liquid adhesive materials 64 and carpule units 17 provided herein. After a new needle 16 is mounted on syringe barrel 14, cover 62 is placed over the needle to ensure sanitary conditions and to avoid inadvertent injection, even though blunt tip 44 is more resistant to injection than a normal syringe needle.

In the example shown herein, the treatment of a tooth begins with a pre-etch of the area to be treated with phosphoric acid gel to remove the surface pellicle and heavily flouridated surface layer. If all of the bonded area is in dentin and instrument enamel, no phosphoric acid pre-etching is necessary. Thereafter, the area to be treated should be isolated and dried and should be protected from moisture contamination while bonding. A drop or two of the NPGHNO$_3$ solution 64 may be then expressed from the unit 10 directly on the tooth and applied with a small cotton pellet, or alternatively may be placed into a dappen dish and applied with a cotton pellet. The entire surface of dentin enamel to be bonded should be scrubbed for approximately 30 seconds and then the solution should be blown away with an air syringe and air dried.

Thereafter, a drop or two of the PMDM-acetone solution 64 should be applied to the tooth with the unit 10 hereof, or alternatively into a dish, and swabbed or brushed on the tooth until the acetone solvent has evaporated. This usually requires 30 to 60 seconds.

The surface is now prepared for application of the composite of choice. If a heavily bonded composite resin is to be used, a thin layer of unfilled resin applied over the dried PMDM will aid in adapting the composite to the surface.

I claim:

1. A delivery system for liquid dental materials, comprising:
  a tubular carpule having a first end and an opposed second fluid delivery end, said second end being provided with puncturable means for permitting selective passage of liquid therethrough, there being a supply of liquid dental material and a bubble of protective gas within said carpule, said bubble presenting a gaseous zone essentially free of liquid when the carpule is held upright with the puncturable means at the upper end of the carpule;
  a tubular syringe barrel separate from said carpule and adapted to receive said carpule therewith;
  application means mounted on said syringe barrel having a forward application end and rearwardly extending tubular structure passing through said puncturable means and in communication with the liquid within said carpule, when said carpule is fully inserted within said syringe barrel from delivery of said liquid from the carpule; and
  shiftable liquid expressing means partially within said carpule and extending rearwardly from the first end of the carpule and said syringe barrel, said expressing means including structure slidably engaged with said carpule for exerting force against said liquid upon shifting of the expressing means to thereby express said liquid through said forward application end,
  said rearwardly extending tubular structure being of sufficient length to pass completely through said gaseous zone and communicate with said liquid material to maintain said bubble during expression of said liquid, whereby expression or leakage of said protective gas from said carpule is inhibited, said forward application end presenting a blunt configuration for preventing injection of said liquid material into a patient.

2. A delivery system as set forth in claim 1, wherein said liquid expressing means includes an elongated plunger situated at least partially within said carpule, the length of said plunger exceeding the length of said carpule.

3. A delivery system as set forth in claim 1, wherein said puncturable means comprises a self-sealing membrane.

4. A delivery system as set forth in claim 3, wherein said membrane is substantially gas and liquid impermeable except when punctured by said application means.

5. A delivery system as set forth in claim 3, wherein said rearwardly extending tubular structure extends at least 1 centimeter rearwardly from said housing and at least 0.5 centimeters rearwardly beyond said membrane into said carpule.

6. A delivery system as set forth in claim 3, wherein said rearwardly extending tubular structure is engaged with said membrane in such manner to require a force of a first magnitude for shifting of said membrane relative to said rearwardly extending tubular structure, and said shiftable liquid expressing means is engaged with said carpule in such manner to require force of a second magnitude for shifting of said expressing means relative to said carpule, said second magnitude being greater than said first magnitude.

7. A delivery system as set forth in claim 1, wherein said blunt end is bent at an oblique angle relative to said rearwardly extending tubular structure.

8. A delivery system as set forth in claim 7, wherein said needle is provided with a housing intermediate said application end and said rearwardly extending tubular structure, said housing including means for releasable connection of the needle to said syringe barrel.

9. The delivery system as set forth in claim 1, said sealing means including one-way valve means mounted adjacent said second delivery end while resisting entry of extraneous substance therethrough.

10. A delivery system for non-injectable, topically applied, liquid dental materials comprising:
a delivery assembly including
a tubular carpule having a first end and an opposed, second liquid delivery end,
sealing means adjacent said delivery end, and
shiftable liquid expressing means partially within said carpule and extending rearwardly from said first end for expressing liquid from said carpule, said expressing means and said carpule cooperatively defining a liquid-receiving space within said carpule;
a supply of non-injectable, topical, liquid dental material and protective gas in the form of a bubble thereof within said liquid-receiving space, said bubble presenting a gaseous zone substantially free of said liquid material;
application means including a forward application end and a rearwardly extending tubular portion for selective topical application of said liquid dental material, said application means including structure mounting said carpule with said application means in an associated relationship with said tubular portion passing through said sealing means and into said space,
said forward application end presenting a blunt configuration for preventing injection of said liquid material,
said tubular portion being of sufficient length to pass completely through said bubble and into communication with said liquid material for maintaining said bubble during expression of said liquid material so that expression or leakage of said protective gas from said carpule is thereby inhibited.

11. The delivery system of claim 10, said mounting structure including a syringe barrel separate from the carpule and adapted to receive the carpule therewithin, said application means including means for releasable attachment thereof to said syringe barrel.

12. The delivery system of claim 10, said mounting structure including clamp means operatively coupled with said delivery end of said carpule.

13. The delivery system of claim 10, said sealing means comprising a puncturable membrane in covering relationship to said delivery end of said carpule.

14. The delivery system of claim 10, said sealing means comprising a one-way check valve located within said rearwardly extending tubular portion.

15. The delivery system as set forth in claim 10, said sealing means including one-way valve means mounted adjacent said second delivery and while resisting entry of extraneous substance therethrough.

16. A method of delivering non-injectable, topical, liquid dental materials comprising the steps of:
providing a delivery assembly including
a tubular carpule having a first end and an opposed, second liquid delivery end,
sealing means adjacent said delivery end, and
shiftable liquid expressing means partially within said carpule and extending rearwardly from said first end for expressing liquid from said carpule, said expressing means and said carpule cooperatively defining a liquid-receiving space within said carpule,
filling said liquid-receiving space with topically applied, liquid dental material and with protective gas in a form of a bubble thereof, said bubble presenting a gaseous zone substantially free of said liquid material when the carpule is held upright with said delivery end as the upper end of said carpule;
providing application means including a forward application end and a rearwardly extending tubular portion for selective topical application of said liquid dental material, said application means including mounting structure for allowing mounting of said carpule with said application means in an associative relationship with said tubular portion passing through said sealing means and into said liquid-receiving space, said forward application end presenting a blunt configuration for preventing injection into a patient;
mounting said carpule in said associative relationship with said application means, said tubular portion being of sufficient length to pass completely through said gaseous zone into communication with said liquid material to maintain said bubble during expression of said liquid material so that expression or leakage of said protective gas from said carpule is thereby inhibited; and
expressing said liquid material by shifting said expressing means toward said delivery end in order to express said liquid material into and through said tubular portion and out said forward application end.

* * * * *